US007253292B2

(12) United States Patent
Nifant'ev et al.

(10) Patent No.: US 7,253,292 B2
(45) Date of Patent: Aug. 7, 2007

(54) SYNTHESIS OF CYCLOPENTADIENE DERIVATIVES

(75) Inventors: Ilya E. Nifant'ev, Moscow (RU); Igor A Kashulin, Moscow (RU); Pavel V. Ivchenko, Moscow (RU); Peter A. A. Klusener, Utrecht (NL); Frans M. Kornorffer, Katvijk aan zee (NL); Kees P. De Kloe, Vlaardingen (NL); Jos J. H. Rijsemus, Harderwijk (NL)

(73) Assignee: Basell Polyolefine GmbH, Wesseling (DE)

( * ) Notice: Subject to any disclaimer, the term of this patent is extended or adjusted under 35 U.S.C. 154(b) by 430 days.

(21) Appl. No.: 10/477,315

(22) PCT Filed: May 8, 2002

(86) PCT No.: PCT/EP02/05094

§ 371 (c)(1),
(2), (4) Date: Nov. 10, 2003

(87) PCT Pub. No.: WO02/092564

PCT Pub. Date: Nov. 21, 2002

(65) Prior Publication Data

US 2004/0236115 A1 Nov. 25, 2004

(51) Int. Cl.
C07D 333/50 (2006.01)
C07D 239/00 (2006.01)
C07D 455/04 (2006.01)

(52) U.S. Cl. .......................... 549/41; 549/42; 549/458; 549/457; 549/43; 548/427; 548/420; 548/421; 548/429; 548/430; 548/302.1; 548/359.5; 546/62; 546/70; 546/80; 546/89; 546/85; 544/250; 544/343; 544/345; 544/247

(58) Field of Classification Search ................ 548/420, 548/427, 428, 429, 430, 302.1, 359.5; 546/81, 546/82, 70, 77, 62, 80, 89, 85; 544/250, 544/343, 345; 549/41, 42, 43, 457, 458
See application file for complete search history.

(56) References Cited

FOREIGN PATENT DOCUMENTS

| EP | 0938491 | 9/1999 |
| WO | 9822486 | 5/1998 |
| WO | 9924446 | 5/1999 |
| WO | 0147939 | 7/2001 |

OTHER PUBLICATIONS

Campo et al, Synthesis of fluorine-9-ones by the palladium-Catalyzed Cyclocarbonylation of o-Haliobiaryls, JOC, 2002, 67(16),5616-5620.*

Kashulin et al, Efficient Method for the Synthesis of Hetarenoindanones Based n 3-Arylhetarenes and Their Conversion into Hetarenoindenes; JOC, 2004, 69(16), 5476-5479.*

M. Iyoda et al., "New Syntheses of Tricyclic Thiophenes and Cyclic Tetrathiophenes using Transition-Metal-Catalyzed Cyclization;" *Heterocycles*, vol. 52(2), p. 761-774 (2000).

"12. Aldehydes and Ketones;" *Comprehensive Organic Transformations*, ed. 1989 VCH Publishers (p. 35-40).

"2. Coupling Reactions;" *Comprehensive Organic Transformations*, ed. 1989 VCH Publishers (p. 45-70).

"2. Aromatic Halogenation;" *Comprehensive Organic Transformations*, ed. 1989 VCH Publishers (p. 315-318).

K. Takagi et al., "Synthesis of Biaryls from Aryl Iodides and Zinc Powder by Means of Nickel Catalyst;" *Chemistry Letters*; p. 917-918 (1979).

B. Krische et al., "Conducting Polymers from Dimethyl-2,2'-bithiophenes;" *J. Chem. Soc., Chem. Commun.*, p. 1476-1478 (1987).

I. Colon et al., "Coupling of Aryl Chlorides by Nickel and Reducing Metals;" *J. Org. Chem.*, vol. 51, p. 2627-2637 (1986).

G. Olah et al., "Synthetic Methods and Reactions; XVIII[1], Preparation of Alkenes via Dehalogenation of vic-Dihaloalkanes, Coupling of Allyl and Benzyl Halides, Dehalogenative Coupling of Aryl-gem-dihaloalkanes using $TiCl_3$- or $TiCl_4/LiAlH_4$ Reagent;" *Synthesis*, p. 607-609 (1976).

A. Suzuki et al., "An Oxygen-Induced Reaction of Trialkylboranes with Alkyl Iodides. A Facile Coupling of Benzylic and Allylic Iodides via Triethylborane;" *J. Am. Chem. Society*, vol. 93(6), p. 1508-1509 (1971).

G. Tolstikov et al., "A New Stereoselective Synthesis of Racemic Disparlure, the Sex Pheromone of Gypsy Moth;" *Tetrahedron Letters*, No. 21, p. 1857-1858 (1978).

J. Kagan et al., "The Synthesis of Bithienyls and Terthienyls by Nickel-Catalyzed Coupling of Grignard Reagents;" *Heterocycles*, vol. 24(8), p. 2261-2271 (1986).

R. Ricke et al., "Direct Preparation of 3-Thienyl Organometallic Reagents: 3-Thienylzinc and 3-Thienyl-magnesium Iodides and 3-Thienylmanganese Bromides and Their Coupling Reactions;" *J. Org. Chem.*, vol. 62(20), p. 6921-6927 (1997).

A. Wiersema et al., "Thiophene analogues of fluorene III. On the synthesis of methylated cyclopentadithiophenes;" *Acta Chemica Scandinavica*, vol. 24(7), p. 2593-2611 (1970).

Weygand-Hilgetag, Organisch-Chemische Experimentierkunst, 3 Neubearbeitete Auflage, Institut fur Organische Chemie der Deutschen Akademie der Wissenschaften zu Berlin (1964) (Index).

* cited by examiner

*Primary Examiner*—Amelia A. Owens
(74) *Attorney, Agent, or Firm*—William R Reid

(57) ABSTRACT

A process for preparing cyclopentadiene derivatives comprising the steps of: a) coupling a five membered heterocycle ring with a five or six membered heterocycle ring; b) reacting the obtained compound with a carbonilating system: c) reducing the obtained compound.

18 Claims, No Drawings

SYNTHESIS OF CYCLOPENTADIENE DERIVATIVES

This application is the U.S. national phase of International Application PCT/EP02/05 094, filed May 8, 2002.

The present invention relates to a process for the preparation of cyclopentadiene derivatives of formula

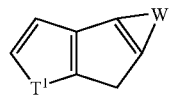

wherein $T^1$ is oxygen, sulphur or a nitrogen radical; W represents a 3 or 4 membered rest that forms a 5 or 6 membered ring. These compounds are fit for the preparation of metallocene complexes useful as catalysts for the polymerization of olefins.

Examples of these cyclopentadiene derivatives are known in the art. WO 98/22486 relates to a class of cyclopentadiene compounds containing heteroatoms used as ligands for metallocene complexes. WO 99/24446, describes bridged and unbridged metallocenes comprising at least a heterocyclic cyclopentadiene group of one of the following formulae:

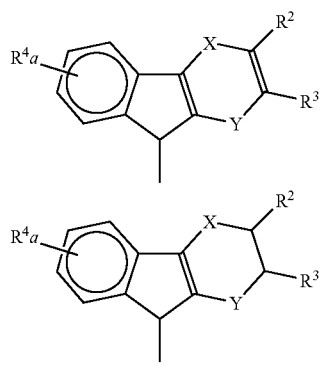

wherein one of X or Y is a single bond, the other being O, S, NR or PR, R being hydrogen or an hydrocarbon group; $R^2$, $R^3$ and $R^4$ are hydrogen, halogen, —R, —OR, —OCOR, —SR, —NR$_2$ or —PR$_2$; a is 0-4. These metallocenes may be used as catalyst components in the polymerization of olefins, particularly in the production of homo and copolymers of ethylene.

A drawback of this kind of metallocene compounds is that the synthesis of the corresponding ligands is not simple inasmuch as it involves several steps leading to low yields.

In WO 01/47939 (PCT/EP00/13191) in the name of the same applicant several synthetic routes have been proposed for obtaining cyclopentadienyldithiophenes compounds. All these routes involve the condensation of two thiophene rings according to the following equation:

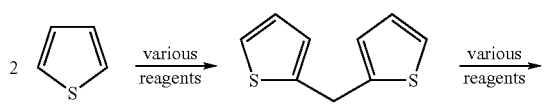

wherein the thiophene rings are substituted with various functional groups.

The same approach has been applied in Heterocycles (2000), 52(2), 761-774 wherein cyclopentadienyldithiophenes have been obtained in moderate to good yields by using the CuCl$_2$ mediated cyclization of organocopper(I), or organozinc intermediates prepared from dilithio-derivatives with CuCN or ZnCl$_2$.

These synthetic routes appear to involve several and complicated steps and often the total yield is unsatisfactory.

Therefore, it would be highly desirable to provide a simple and more efficient route to the preparation of this class of cyclopentadienyl compounds.

The applicant has surprisingly found that by reversing the order of condensation (i.e. in the case of cyclopentadithiophene: firstly coupling of the two thiophene rings in position 3 and then closing the cyclopentadiene ring in position 2) it is possible to obtain higher yields with a simpler process. Moreover this process can also be advantageously used for obtaining a broader class of compounds.

An object of the present invention is a process for preparing cyclopentadiene derivatives having formula (I)

(I)

wherein $T^1$ is selected from the group consisting of oxygen (O), sulphur (S) and NR, wherein R is a linear or branched saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements;

$R^1$, $R^2$, equal to or different from each other, are hydrogen or a linear or branched saturated or unsaturated $C_1$-$C_{20}$-alkyl, $C_3$-$C_{20}$-cycloalkyl, $C_6$-$C_{20}$-aryl, $C_7$-$C_{20}$alkylaryl or $C_7$-$C_{20}$-arylalkyl radical, optionally containing heteroatoms belonging to groups 13-17 of the Periodic Table of the Elements; or they can form a $C_4$-$C_7$ ring optionally containing O, S, N, P or Si atoms that can bear substituents;

W is a moiety (a) or (b)

(a)

(b)

wherein $T^2$, $T^3$, $T^4$, $T^5$, equal to or different from each other, are selected from the group consisting of nitrogen (N) and $CR^3$ wherein $R^3$ is hydrogen or a linear or branched saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; or two adjacent $R^3$ groups can form a $C_4$-$C_7$ ring optionally containing O, S, N, P or Si atoms, said ring can bear substituents; preferably not more than two groups selected from $T^2$, $T^3$, $T^4$, $T^5$ are nitrogen at the same time;

$T^6$ has the same meaning as $T^1$;

$T^7$ and $T^8$, equal to or different from each other, are selected from N and $CR^3$ wherein $R^3$ is hydrogen or a linear or branched saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; optionally two adjacent group $R^3$ can form a $C_4$-$C_7$ ring optionally containing O, S, N, P or Si atoms, said ring can bear substituents; with the proviso that when $T^6$ is different from NR, $T^7$ and $T^8$ are both $CR^3$;

preferably when $T^6$ is NR, at least one group between $T^7$ and $T^8$ is $CR^3$;

said process compres the following steps:

a) reacting a compound of formula (II)

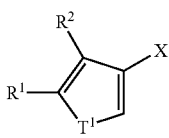
(II)

with a compound of formula (III)

(III)

in the presence of a coupling system, wherein W, $T^1$, $R^1$ and $R^2$, have the above indicated meaning and X is selected from the group consisting of chlorine, iodine, bromine; preferably X is bromine;

b) contacting the compound of formula (IV)

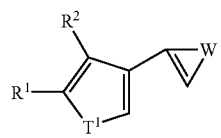
(IV)

obtained from step a) with a carbonylating system; in order to obtain a compound of formula (IVa)

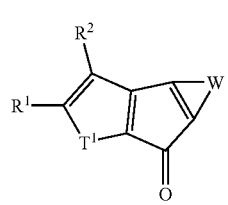
(IVa)

and c) treating the product obtained in step b) with a reducing agent.

When W is a moiety of formula (a)

(a)

a preferred process for preparing the cyclopentadiene compounds of formula (Ia)

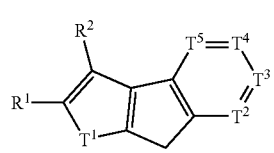
(Ia)

wherein $T^1$, $T^2$, $T^3$, $T^4$, $T^5$, $R^1$ and $R^2$ have the above indicated meaning comprises the following steps:

a) reacting a compound of formula (II)

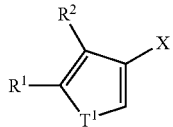
(II)

with a compound of formula (V)

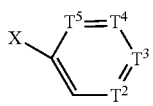
(V)

in the presence of a coupling system,
wherein $T^1$, $T^2$, $T^3$, $T^4$, $T^5$, $R^1$ and $R^2$, have the above reported meaning and X is select from the group consisting of chlorine, iodine, bromine; preferably X is bromine;

b) contacting the compound of formula (VI) obtained from step a)

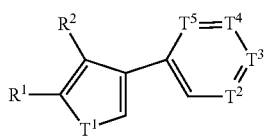
(VI)

with a carbonylating system; in order to obtain a compound of formula (VIa)

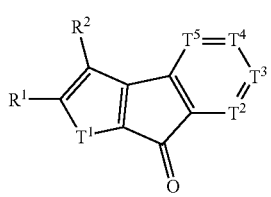
(VIa)

and
c) treating the product obtained in step b) with a reducing agent.

When W is a moiety of formula (b)

(b)

a preferred process for preparing the cyclopentadiene compounds of formula (Ib)

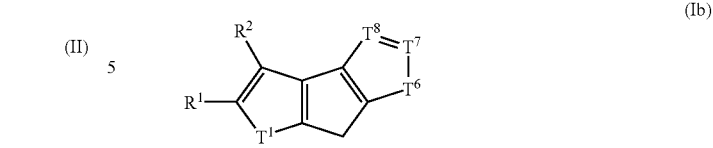
(Ib)

wherein $T^1$, $T^6$, $T^7$, $T^8$, $R^1$ and $R^2$ have the above described meaning comprises the following steps:

a) reacting a compound of formula (II)

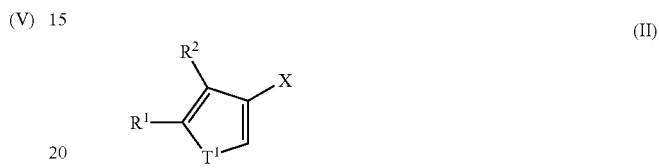
(II)

with a compound of formula (VII)

(VII)

in the presence of a coupling system, wherein $T^1$, $T^6$, $T^7$, $T^8$, $R^1$ and $R^2$, have the above described meaning, and X is selected from the group consisting of chlorine, iodine, bromine; preferably X is bromine;

b) contacting the compound of formula (VIII) obtained from step a)

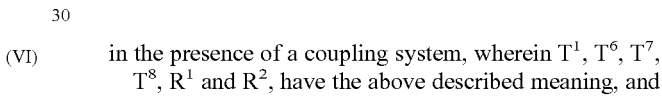
(VIII)

with a carbonylating system; in order to obtain a compound of formula (VIIIa)

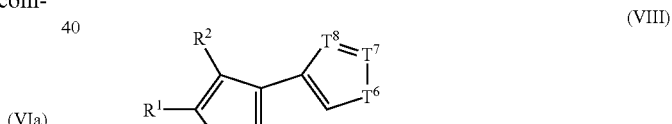
(VIIIa)

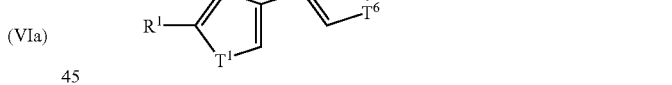

and;
c) treating the product obtained in step b) with a reducing agent.

For the purpose of the present invention the coupling system is a reagent or a series of reagents that in one or more steps can couple the two compounds of steps a) in order to form the compound of formula (IV). Examples of coupling systems can be found in "Comprehensive Organic Transformations" ed. 1989 VCH Publishers pages 45-70. Below is an illustrative non limiting list of coupling systems and relevant references.

| Coupling system | Reference |
|---|---|
| Zn, NiBr$_2$, KI | Chem. Lett. 917 (1979) |
| Zn, NiCl$_2$(PPh$_3$)$_2$, n-Bu$_4$NI | J. Chem. Soc.: Chem. Commun. 1476 (1987) |
| Zn, Mg or Mn; cat NiCl$_2$; PPh$_3$ | J. Org. Chem. 51 2627 (1986) |
| TiCl$_3$ or TiCl$_4$, LiAlH$_4$ | Synthesis 607 (1976) |
| O$_2$, Et$_3$B | J. Am. Chem. Soc. 93 1508 (1971) |
| RMgBr + R'Br → R—R' | Tetrahedron Lett. 1857 (1978) |

The amount of the coupling system used depends obviously on the type. Generally it is used at least one equivalent of coupling system.

A preferred step a) comprises the following substeps:
i) contacting the compound of formula (II) with magnesium to form the correspondent Grignard reagent;
ii) contacting the Grignard reagent formed in step i) with the compound of formula (III) in the presence of a compounds selected from the group consisting of [1,3-bis (diphenylphosphino)propane]dichloronickel (dpppNiCl$_2$), [1,1'-bis(diphenylphosphino)ferrocene] dichloropalladium (dppfPdCl$_2$), tetrakis (triphenylphosphino)palladium; preferably with dpppNiCl$_2$.

Alternatively step a) comprises the following substeps
i) contacting the compound of formula (III) with magnesium to form the correspondent Grignard reagent;
ii) contacting the Grignard reagent formed in step i) with the compound of formula (II) in the presence of a compounds selected from the group consisting of [1,3-bis(diphenylphosphino)propane]dichloronickel (dpppNiCl$_2$), [1,1'-bis(diphenylphosphino)ferrocene]dichloropalladium (dppfPdCl$_2$), tetrakis(triphenylphosphino)palladium; preferably with dpppNiCl$_2$.

The Grignard reagents are obtained with process known in the art such as those cited by Kagan et al. (Heterocycles, 1986, 2261) or Riecke et al. (J. Org. Chem., 1997, 6921). The preferred process uses magnesium activated by 10% of dibromoethane in tetrahydrofuran as described in Weygand-Hilgetag, Organisch-Chemische Experimentierkunst, 3 Auflage, 1964. When W is equal to the moiety (b) and the compounds of formula (II) and (III) are the same a further preferred step a) comprises contacting two equivalents of the compound of formula (II) with a coupling system comprising
i) an alkali or alkaline earth-metal, preferably zinc (zinc powder or granules (mossy zinc));
ii) a compound of formula QG$_3$ or a compound of formula G$_2$Q-A-QG$_2$ wherein Q is a phosphorus or nitrogen atom, G equal to or different from each other are selected from the group consisting of linear or branched saturated or unsaturated C$_1$-C$_{20}$-alkyl, C$_3$-C$_{20}$-cycloalkyl, C$_6$-C$_{20}$-aryl, C$_7$-C$_{20}$-alkylaryl, C$_7$-C$_{20}$-arylalkyl radical, optionally containing heteroatoms belonging to groups 13-17 of the Periodic Table of the Elements and A is a group linking the two Q atoms; it can be a divalent organic radical selected from the group consisting of C$_1$-C$_{20}$-alkylene, C$_3$-C$_{20}$-cycloalkylene, C$_2$-C$_{20}$-alkenylene, C$_6$-C$_{20}$-arylene C$_7$-C$_{20}$-alkylarylene, C$_7$-C$_{20}$-arylalkylene divalent radical, optionally containing heteroatoms belonging to groups 13-17 of the Periodic Table of the Elements; A can be also a different group such as a complex that has the two radicals G$_2$Q as substituents such as a ferrocene group to form for example 1,1'-bis (diphenylphosphino)ferrocene; preferably the compound used has formula QG$_3$; wherein preferably Q is phosphorous and at least one G is phenyl or a substituted phenyl, more preferably QG$_3$ is triphenylphosphine; and
iii) a transition metal halogenide of formula JZ$_e$ wherein J is a transition metal, preferably it is a transition metal of groups 4-11 of the periodic table, Z is chlorine, bromine, iodine and e is equal to the oxidation state of the metal J, preferred compound of formula JZ$_e$ is NiBr$_2$.

Step a) is carried out at a temperature range of from −78 C. to 100° C., preferably from 10° C. to 60° C. Usually aprotic solvents are used, such as toluene, diethyl ether, hexane, tetrahydrofuran, dimethyl formamide, etc. The product obtained from step a) is purified by process known in the art such as filtration, crystallization, chromatography, distillation; otherwise it is used as such.

For the purpose of the present invention the carbonylating system is defined as reagent or a series of reagents that in one or more steps can close the five membered ring in order to obtain compound of formula (IVa). Carbonylating step b) depends from the carbonyl system used. A preferred step b) comprises the following substeps:
i) contacting the compound of formula (IV) obtained from step a) with two equivalents of a base; and
ii) treating the dianionic compound obtained from step i) with a compound of formula (IX)

(IX)

wherein R$^4$ and R$^5$ equal to or different from each other are selected from the group consisting of hydrogen, chlorine, bromine, iodine, OR and NR$_2$, wherein R is described above; preferably R$^4$ is chlorine bromine, iodine CF$_3$, Cl$_3$ or OR, more preferably chlorine or OCH$_2$CH$_3$; preferably R$^5$ is selected from the group consisting of CF$_3$, Cl$_3$, OR and NR$_2$, wherein R is described above, more preferably R$^5$ is NR$_2$, even more preferably R$^5$ is N(CH$_3$)$_2$;

An alternative embodiment for carrying out step b) comprises the following substeps:
i) contacting the compound of formula (IV) obtained from step a) with two equivalents of a base and subsequently with one equivalent of a compound selected from chlorine, bromine or iodine in order to obtain an anionic monohalogenated derivative; and
ii) treating the an anionic monohalogenated compound obtained from step i) with a compound of formula (IXa)

(IXa)

wherein M is a transition metal of groups 4-11 of the periodic table; L is a ligand that coordinates the metal M that can be neutral or with a positive or negative charge; a ranges from −4 to +4, it represents the charge of the complex when a is 0 the complex is neutral; m ranges from 1 to 20; j ranges from 0 to 30; and n ranges from 1 to 50; preferably a ranges from −2 to +2; m ranges from 1 to 10; j ranges from 0 to 5 and n ranges from 1 to 20.

A further alternative embodiment for carrying out step b) comprises the following substeps:

i) contacting the compound of formula (IV) obtained from step a) with a halogenating compound and subsequently with one equivalent of a base in order to obtain an anionic monohalogenated derivative; and ii) treating the an anionic monohalogenated compound obtained from step i) with a compound of formula (IXa)

[M$_m$L$_j$(CO)$_n$]$^a$ (IXa)

wherein M is a transition metal of groups 4-11 of the periodic table; L is a ligand that coordinates the metal M that can be neutral or with a positive or negative charge; a ranges from −4 to +4, it represents the charge of the complex when a is 0 the complex is neutral; m ranges from 1 to 20; j ranges from 0 to 30; and n ranges from 1 to 50; preferably a ranges from −2 to +2; m ranges from 1 to 10; j ranges from 0 to 5 and n ranges from 1 to 20.

The base used in step b) is preferably selected from hydroxides and hydrides of alkali- and alkaline-earth metals, metallic sodium and potassium and organometallic lithium compounds. Most preferably, said bases are methyllithium, n-butyllithium, or tertbutyllithium optionally activated with tetramethylethylene diamine (TMEDA).

Example of halogenating compounds are described in "Comprehensive Organic Transformations" ed. 1989 VCH Publishers pages 315-318, such as for example chlorine, bromine, iodine CuCl$_2$, CBr$_4$, N-bromo-succinimide, N-chloro-succinimide. Non limitative example of compounds of formula (IX) are:

carbethoxyimidazole, triphosgene, ethyl N,N-dimethylcarbamate, chloride of N,N-dimethylcarbamic acid.

Non limitative example of ligands L are; halogen, hydrogen, nitrogen, amines, phosphine, cyclopentadienyl derivatives, octadienes.

Non limitative example of compound of formula (IXa) are C(CO)$_6$, Cr(CO)$_6$, Cr(CO)$_5$H$_2$, Mn(CO)$_5$H, Mn(CO)$_5$I, Mn$_2$(CO)$_{10}$, Mn$_2$(CO)$_8$H$_2$Fe(CO)$_5$,
Fe(CO)$_4$H$_2$, Fe(CO)$_2$X$_2$, Fe(CO)$_4$X$_2$, Fe(CO)$_5$X$_2$, Fe$_2$(CO)$_9$, Co(CO)$_4$H,Co(CO)$_2$X$_2$,
Co(CO)$_4$X$_2$, Co(CO)$_5$X$_2$, Co$_2$(CO)$_6$, Ni(CO)$_4$, Ni$_2$(CO)$_6$H$_2$, Fe$_3$(CO)$_{12}$,[Fe(CO)$_{11}$H]$^-$,
Os$_3$(CO)$_{12}$, [Re$_3$(CO)$_{12}$H$_6$]$^-$, [Re$_4$(CO)$_{16}$]$^{2-}$, Co$_4$(CO)$_{12}$, [Fe$^4$(CO)$_{13}$]$^{2-}$, $^{Os}$$_5$(CO)$_{16}$,
[Os$_5$(CO)$_{15}$I]$^-$, [Ni$_5$(CO)$_{12}$]$^{2-}$, [Fe$_5$C(CO)$_{15}$]$^-$, Rh$_6$(CO)$_{16}$, Rh$_6$(CO)$_{15}$I, [Co$_6$(CO)$_{14}$]$^{4-}$,
[Fe$_6$C(CO)$_{16}$]$^{2-}$, [Co$_6$H(CO)$_{15}$]$^-$, [Rh$_6$C(CO)$_{15}$]$^{2-}$, [Co$_6$N(CO)$_{15}$]$^-$, Os$_6$(CO)$_{18}$;
wherein X is chlorine, bromine, iodine.

Step b) is carried out to a temperature range of from −78 C. to 100° C. preferably from −20° C. to 30° C. Usually aprotic solvents are used such as diethyl ether, hexane, toluene, tetrahydrofuran, dimethoxyethane and dioxane. The product obtained from step b) is purified by process known in the art such as filtration, recrystallization, chromatography, distillation; or alternatively is used as such.

In step c) various reducing agent known in the art can be used. Example of suitable reducing agent used in step c) are described in "Comprehensive Organic transformations" ed. 1989 VCH Publishers pages 35-40. Preferred reducing agents are LiAlH$_4$/AlCl$_3$ and N$_2$H$_4$/base, such as NaOH and KOH.

The solvent for carrying out step c) depends upon the reducing agent used. For example when LiAlH$_4$/AlCl$_3$ is used the reaction is carried out is an aprotic solvent either polar or apolar such as tetrahydrofuran, dimethoxyethane, diethyl ether, toluene, pentane, hexane. When N$_2$H$_4$/base is used a protic solvent such as water or diethylene glycol can also be used, optionally in the presence of a phase transfer agent. The temperature depends from the reducing agent used, it generally ranges from −80 C. to 300 C., preferably from 0° C. to 150 C.

Preferably the step c) comprises the following substeps:

i) contacting the compound of formula (VIa) with N$_2$H$_4$;

ii) adding a solution of KOH in water; and iii) filtering the solid and recovering the product.

Step i) is preferably carried out in water, toluene or diethylene glycol; step ii) is preferably carried out in the presence of a phase transfer agent, preferably diethylene glycol.

The product obtained from step c) is purified by process known in the art such as filtration, crystallization, column chromatography, preferably by filtration.

In the compound of formula (Ia):

T$^1$ is preferably sulphur or oxygen, more preferably is sulphur; T$^2$ is NCH$_3$ or CH, more preferably CH; T$^3$, T$^4$, T$^5$ are preferably CH;

R$^1$ and R$^2$ are preferably hydrogen methyl, ethyl, phenyl, trimethylsilyl group or together form a benzene ring; more preferably R$^1$ is methyl and R$^2$ is hydrogen or together form a benzene ring;

In the compound of formula (Ib) preferably:

T$^1$ and T$^6$ are the same and they are sulfur or oxygen, more preferably they are sulfur;

T$^7$ and T$^8$ equal to or different from each other are preferably CR$^3$; more preferably T$^8$ is CH or form with T$^7$ a benzene ring;

T$^7$ is preferably hydrogen C—CH$_3$, C—CH$_2$CH$_3$, C—C$_6$H$_5$, Csi(CH$_3$)$_3$ or form with ring, more preferably T$^7$ is C—CH$_3$ or form with T$^8$ a benzene ring;

R$^1$ and R$^2$ are preferably hydrogen methyl, ethyl, phenyl, trimethylsilyl group or together form a benzene ring; more preferably R$^1$ is methyl and R$^2$ is hydrogen or together form a benzene ring;

Non limitative examples of compounds of formula (I) are:

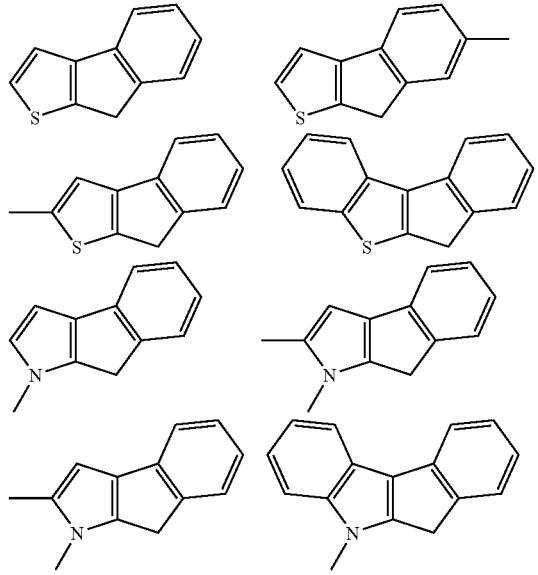

-continued

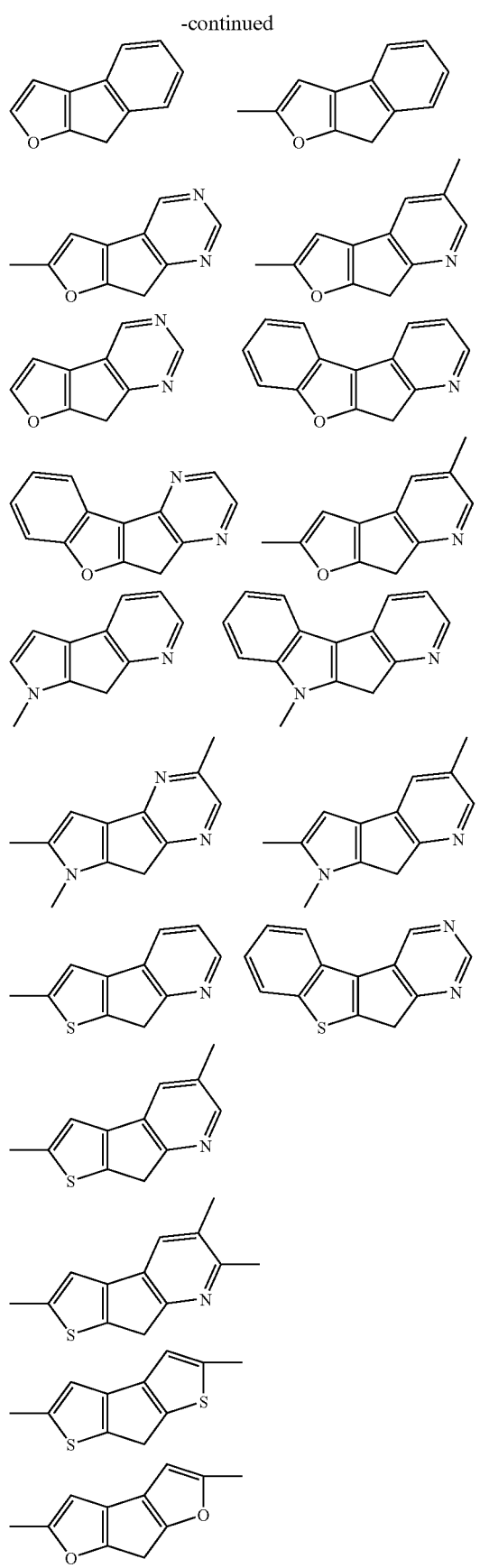

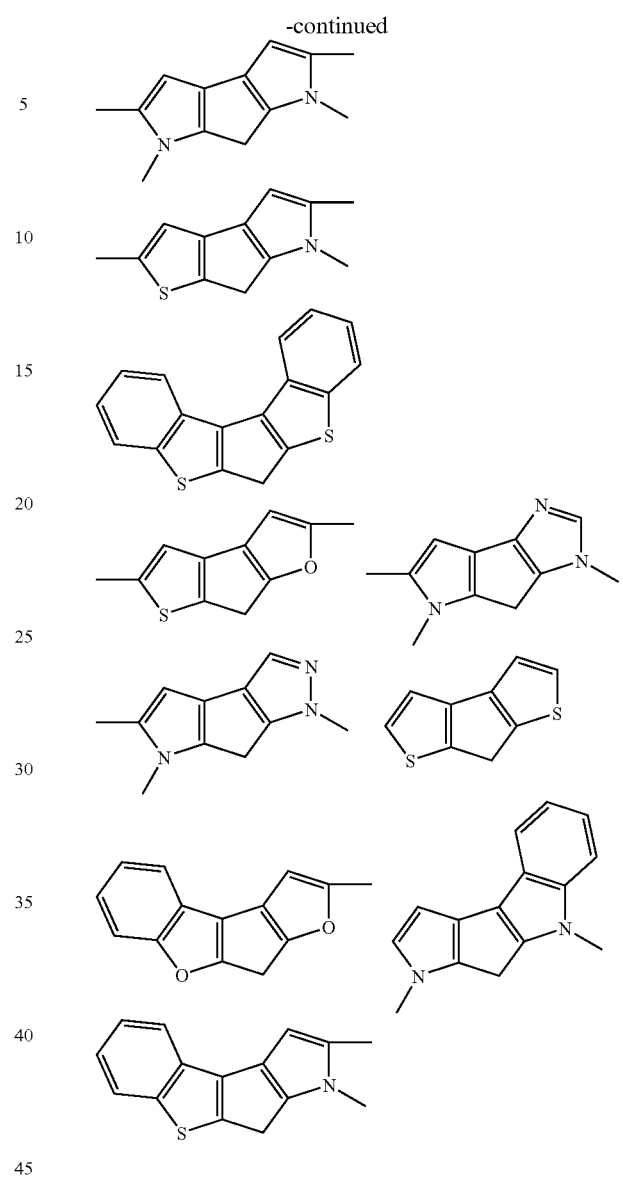

Compounds of formula (II) and (III) are commercially available or can be obtained with processes known in the art, in particular compounds of formula (II) are described in WO 98/22486, WO 99/24446 PCT/EP00/13191, and EP 938491.

Compounds of formula (I) can be used as ligands for the synthesis of metallocene complexes, such as those described in WO 98/22486 WO 99/24446 and PCT/EP00/13191. These complexes are useful as catalyst components for polymerizing alpha-olefins. The syntheses of the metallocene compounds starting from the compounds of the present invention are described in the above mentioned applications. Generally, the compounds of formula (I) can be treated with a base and then contacted with a compound of formula YL'Cp wherein Y is halogen, preferably chlorine, L' is a suitable bridge and Cp is a substituted or unsubstituted cyclopentadienyl radical. The obtained bridged ligand is then treated with two equivalents of a base and contacted with the compound of formula $ML''_4$ wherein M is titanium, zirconium or hafnium and L is generally halogen, preferably chlorine. For unbridged metallocene compounds the compound of formula (I) is treated with a base and then the correspondent anion is contacted with a compound of formula ML"$_4$.

A further object of the present invention is a compound of formula (X)

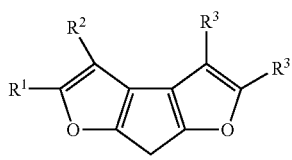

wherein $R^1$, $R^2$ and $R^3$ have been described above with the proviso that at least one $R^1$, $R^2$ or $R^3$ is different from hydrogen.

A still further object of the present invention is a compound of formula (XI)

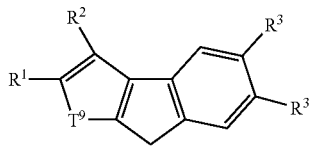

wherein $R^1$, $R^2$ and $R^3$ have been described above and $T^9$ is O (Oxygen) or S (sulphur).

The following examples are given for illustrative purposes and are not intended to limit the scope and spirit of the invention.

EXAMPLES

General Procedures.

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. n-BuLi (Aldrich) was used as received.

Synthesis of ethyl N,N-dimethylcarbamate

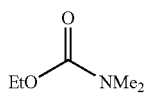

85 mL (0.89 mol) of ethyl chloroformate was added dropwise to 500 mL 33% aqueous dimethylamine at 0-10° C. within 1.5 h. Resulting mixture was stirred in 4 hours, and then it was extracted with methylene chloride (4 portions of 250 mL). The extracts were washed with water, 5% HCl, 3% KHCO$_3$, with water again and finally was dried by MgSO$_4$. The solution was evaporated and distilled at 144° C. to give 84 g (80%) of the product.

$^1$H NMR (CDCl$_3$): 4.12 (q, 2H); 2.90 (br.s., 6H); 1.25 (t, 3H)

$^{13}$C NMR (CDCl$_3$): 156.6; 60.8; 35.9 (br.s); 35.4(br.s); 14.4

Synthesis of 4-bromo-2-methylthiophene i) Bromination of 2-thiophenecarboxaldehyde

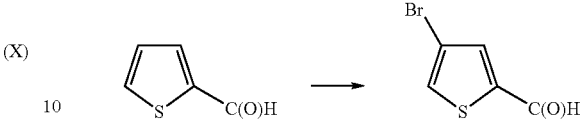

668 g (5 mol) of AlCl$_3$ were suspended in 1 L of chloroform. 224 g (2 mol) of 2-thiophenecarboxaldehyde (Lancaster of 98% purity) were added dropwise within 1 hour to the cooled resulting mixture under stirring. The suspension was stirred 1 hour, then 114 mL (2.2 mol) of Br$_2$ were added dropwise in 1.5 h and the reaction was stirred overnight.

The resulting mixture was poured into the beaker with 1 kg ice and 200 mL of 32% HCl under stirring. The organic phase was isolated, washed with water, then with 5% aqueous NaHCO$_3$, then with 5% aqueous, then with water again. The resulting solution was dried with MgSO$_4$ and evaporated. The 4-bromo-2-thiophenecarboxaldehyde crystallises spontaneously. It was used without further purification. Yield 80-86%.

$^1$H NMR (CDCl$_3$): 9.88 (d, 1H); 7.69(d, 1H); 7.66 (t, 1H).
$^{13}$CNMR (CDCl$_3$): 181.4; 143.6; 137.5; 131.9; 111.1 ii) Reduction of 4-bromo-thiophenecarboxaldehyde

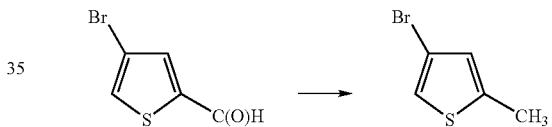

191 g (1 mol) of 4-bromo-2-thiophenecarboxaldehyde, 500 mL of diethylene glycol and 146 mL (3 mol) of hydrazine monohydrate were placed in a bulb. This suspension was refluxed for 1 h and then cooled to room temperature. The resulting mixture was treated with a solution of 342 g (6 mol) of KOH in 400 mL of water. The mixture was carefully heated to reflux and after evolution of nitrogen is over the product was distilled with water from the reaction-bulb. The so distilled two-phase mixture was treated with 200 mL of CH$_2$Cl$_2$, organic phase was isolated, washed twice with water, dried over MgSO$_4$, evaporated and distilled at 60-64° C./10 torr. Total yield ca. 70% for two steps starting from 2-thiophenecarboxaldehyde.

$^1$H NMR (CDCl$_3$): 7.02 (d, 1H); 6.73 (q, 1H); 2.52 (d, 3H)
$^{13}$C NMR (CDCl$_3$): 141.0; 127.7; 120.2; 108.9; 15.2

Synthesis of 4-bromo-2-methylthiophene (alternative route)

i) 4-bromothiophenecarboxaldehyde

A mixture of 119 g (892 mmol) of AlCl$_3$ was suspended into 150 mL of dichloromethane. To this mixture was added 66.6 g (595 mmol) of 2-thiophenecarboxaldehyde in a way the temperature raised to reflux. After addition the mixture was stirred for 30 minutes at room temperature. Then 33.8 mL (654.5 mmol) of Br$_2$ was added and the mixture was stirred overnight and poured into a mixture of 250 g of ice and 50 mL of concentrated HCl. The organic layer was isolated and washed subsequently with 300 mL of 5 w % NaHCO₃ and 300 mL of 5 w % aqueous KOH. The organic layer was isolated, dried over MgSO₄ and concentrated in vacuo. The resulting solid (115 g, crude yield 100%) contained 94% of 4-bromo-2-thiophenecarboxaldehyde, 5% of 4,5-dibromo-2thiophenecarboxaldehyde and 1% of starting material.

ii) 4-bromo-2-methylthiophene

To 1.3 mL (26.2 mmol) of hydrazine monohydrate was added 5 g (26.2 mmol) of 4-bromo-2-thiophenecarboxald in 5 mL of toluene at 90° C. After 1 h stirring at this temperature 1.7 g (26.2 mmol) of KOH was added as a solid and 2 mL of diethylene glycol was added subsequently. Gas formation was noticed. After 2 h the reaction was complete. The toluene layer was isolated and the glycol layer was extracted twice with 5 mL of toluene, yielding 5.6 g of 71 w % solution of 4-bromo-2-methylthiophene. The contained yield was 86% (according to ¹H-NMR) and the purity 97%. The product contained still 2% of 4,5-dibromo-2-methylthiophene.

iii) 4-bromo-2-methylthiophene (alternative process)

A reactor equipped with stirrer, reflux condenser and thermometer was loaded with 392 g (1.97 mol) of 4-bromo-2-thiophenecarboxaldehyde and 220 g (12.2 mol) of water. This slurry was heated to 100° C. The 4-bromo-2-thiophenecarboxaldehyde melted and a suspension was formed under stirring. At this temperature 106 g (2.07 mol) of hydrazine monohydrate was dosed to the mixture over a period of 30 min. An exotherm was observed and the mixture was refluxing. After 1 h post reaction time at 100° C., 353 g (3.3 mol) of diethylene glycol was added slowly. Hereafter a solution of 116 g (2.1 mol) of KOH in 135 g of water was dosed slowly (1 h) to the reaction mixture. After 10% of the base was added slow evolution of gas (nitrogen) was observed from the reaction mixture. After the KOH/water addition, the mixture was kept at 100° C. for 24 h while stirring. Hereafter the mixture was allowed to cool to ambient temperature and the phases were separated. The organic phase was washed twice with 100 g of water. Analyses of the organic layer showed complete conversion and a product purity of the formed 4-bromo-2-methylthiophene of 98%. The yield was 98%.

Example 1

Synthesis of 2-methyl-8H-indeno[2,1-b]thiophene

Step a) 2-methyl-4-phenylthiophene

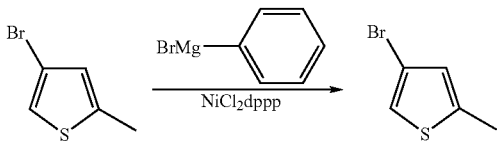

A solution of PhMgBr (prepared from 1.65 g of Mg (0.0678 mol) and 10.64 g of PhBr (0.0678 mol) in 40 mL of diethyl ether) was added to a mixture of 10 g (0.0565 mol) of 4-bromo-2-methylthiophene and 0.62 g (0.0012 mol) of NiCl₂dppp in 50 mL of ether under stirring at reflux. The reaction mixture was refluxed for additional 3 h and then stirred overnight. The resulting mixture was treated with 10% aqueous NH₄Cl, the organic layer was separated, washed with 10% aqueous NH₄Cl and then dried with anhydrous Na₂SO₄. Solvent was evaporated, the residue was recrystallized from methanol. Yield 6.8 g (70%) of colorless crystals.

¹H NMR (CDCl₃, 30° C.) d: 7.65 (d, 2H), 7.47 (d, 2H), 7.37 (t, 1H), 7.28 (m, (s, 1H).

Step b) 2-methyl-8H-indeno[2,1-b]thiophen-8-one

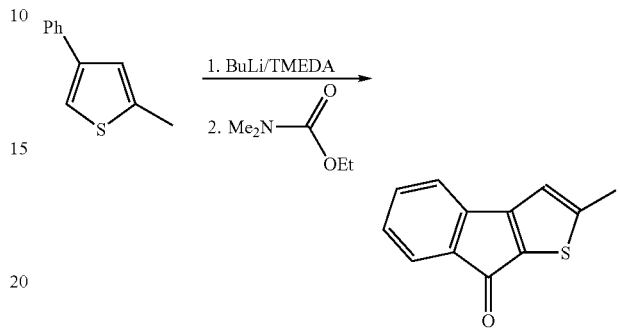

A solution of 12.88 g (0.074 mol) of 2-methyl-4-phenylthiophene, 23.4 mL (0.16 mol) of TMEDA in 200 mL of diethyl ether (ether) was treated with 100 mL (0.16 mol) of 1.6M BuLi in hexane under stirring at −40° C. Then the reaction mixture was allowed to warm up to room temperature (r.t.) and was stirred for 3 h (white precipitate forms). The reaction mixture was cooled to −40° C. and treated with 8.76 g (0.075 mol) of ethyl N,N-dimethylcarbamate in 25 mL of ether. Then the reaction mixture was allowed to warm up to r.t. and was stirred overnight. Resulting mixture was treated with 10% aqueous NH₄Cl, the organic layer was separated and the organic phase was washed with 10% aqueous solution of NH₄Cl and then dried by anhydrous Na₂SO₄. Solvent was evaporated and the residue was washed with methanol. Yield 6.8 g (46%) of red crystals.

¹H NMR (CDCl₃, 30° C.) d: 7.44 (d, 1H), 7.29 (t, 1H), 7.14 (t, 1H), 7.07 (d, 2.55 (s, 3H).

step c) 2-methyl-8H-indeno[2,1-b]thiophene

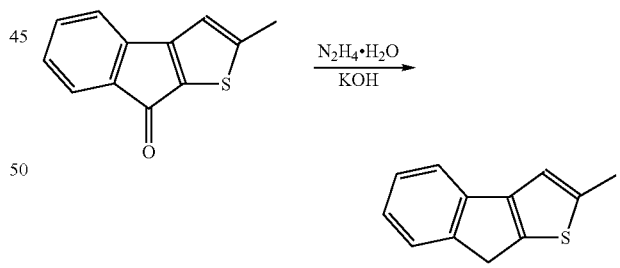

A mixture of 6.83 g (0.034 mol) of 2-methyl-8H-indeno[2,1-b]thiophen-8-one and 9.1 mL (0.182 mol) of hydrazine monohydrate in 91 mL of diethylene glycol was stirred at 80° C. for 40 min and then refluxed for 1 h. The resulting mixture was cooled to room temperature, treated with a solution of 9.5 g (0.169 mol) of KOH in 34 mL water and then refluxed for 2 h.

The resulting mixture was poured into 600 mL of water, the precipitate was filtered, washed 5 times with 200 mL of water and dried. Yield 5.8 g (92%).

¹H NMR (CDCl₃, 30° C.) d: 7.53 (d, 1H), 7.51 (d, 1H), 7.37 (t, 1H), 7.23 (t, 7.01 (m, 1H), 3.81 (s, 2H), 2.61 (s, 3H).

Example 2

Synthesis of 5,8-dimethyl-5,6-dihydroindeno[2,1-b]indole 3-bromo-1-methyl-1H-indole A solution of 1.2 mL (0.0229 mol) of $Br_2$ in 40 mL of pyridine was added to a solution of 3.0 g (0.0229 mol) of N-methylindole in 30 mL of pyridine. The reaction mixture was stirred for 1 h, then it was treated with 100 mL of cold ether and the suspension was filtered. Cold solution was washed with 100 mL of 5% aqueous NaOH, with water (50 mL) and finally was dried over anhydrous sodium sulfate. The resulting solution was evaporated to give 4.31 g (89%) of product as brown oil.

$^1$H NMR (CDCl$_3$, 25° C.) δ: 7.50 (d, 1H); 7.40 (m, 2H); 7.26 (m, 1H); 7.08 (s,1H); 3.77 (s, 3H).

step a) 1-methyl-3-(4-methylphenyl)-1H-indole

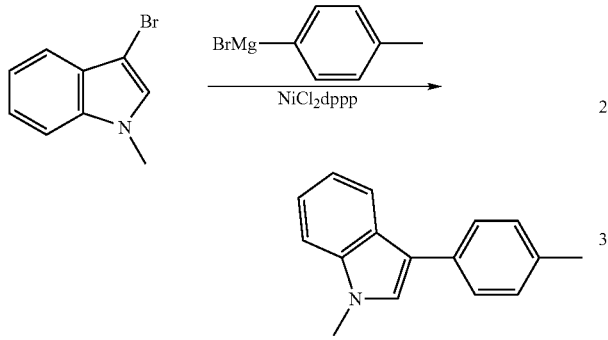

A mixture of 4.31 g (0.02 mol) of 3-bromo-1-methyl-1H-indole and 0.22 g (0.0004 mol) of NiCl$_2$dppp was added to a solution of p-TolylMgBr in ether (prepared from 0.6 g of Mg (0.025 mol) and 4.21 g of TolylBr (0.024 mol) in 40 mL of ether) under stirring. The reaction mixture was stirred overnight. The resulting mixture was treated with 10% aqueous NH$_4$Cl, the organic layer was separated, washed with 10% aqueous NH$_4$Cl and then dried over anhydrous Na$_2$SO$_4$. The solution was evaporated to give an oil that crystallized. The product was washed with methanol and dried. Yield 2.2 g (49%) of colorless crystalline solid.

$^1$H NMR (CDCl$_3$, 25° C.) δ: 8.14 (d, 1H); 7.75 (d, 2H); 7.44 (m, 5H); 7.26 (m, 1H); 3.90 (s, 3H); 2.58 (s, 3H).

step b) 5,8-dimethylindeno[2,1-b]indol-6(5H)-one

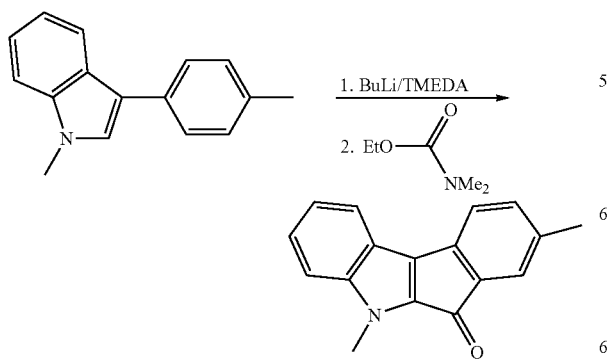

A solution of 2.19 g (0.00991 mol) of 1-methyl-3-(4-methylphenyl)-1H-indole and 3.24 mL (0.0218 mol) of TMEDA in 30 mL of ether was treated with 13.6 mL (0.0218 mol) of 1.6M BuLi in hexane under stirring at −40° C. Then the reaction mixture was allowed to warm up to r.t. and stirred for 4 h. The reaction mixture was cooled to −60° C. and treated with 1.16 g (0.00991 mol) ethyl N,N-dimethylcarbamate in 5 mL of ether. Then the reaction mixture was allowed to warm up to r.t. and was stirred overnight. Resulting mixture was treated with 50 mL of 10% aqueous NH$_4$Cl. The violet precipitate was separated, washed twice with water and dried. Yield 1.04 g (42%).

$^1$H NMR (CDCl$_3$, 25° C.) δ: 7.58 (d, 1H); 7.27 (t, 1H); 7.22 (d, 1H); 7.14 7.09 (s, 1H); 6.98 (d, 1H); 6.92 (d, 1H); 3.80 (s, 3H); 2.26 (s, 3H).

Step c) 5,8-dimethyl-5,6-dihydroindeno[2,1-b]indole

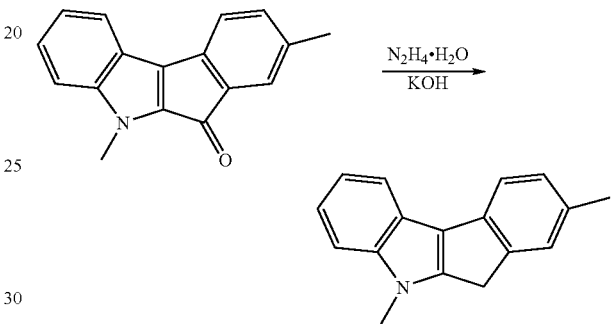

A mixture of 1.04 g (0.0042 mol) of 5,8-dimethylindeno[2,1-b]indol-6(5H)-one and 1.12 mL (0.0224 mol) of hydrazine monohydrate in 20 mL of diethylene glycol was stirred at 80° C. for 1 h and then refluxed for 1 h. The resulting mixture was cooled to r.t., treated with a solution of 1.2 g (0.0214 mol) of KOH in 5 mL of water and then it was refluxed for 2 h. The resulting mixture was poured into 100 mL of water, the precipitate was filtered, washed 5 times with 50 mL of water and dried. Yield 0.84 g (86%) of greenish solid.

$^1$H NMR (CDCl$_3$, 25° C.) δ: 7.88 (m, 1H); 7.55 (d, 1H); 7.36 (m, 1H); 7.26 3H); 7.18 (d, 1H); 3.77 (s, 3H); 3.64 (s, 2H); 2.44 (s, 3H).

Example 3

Synthesis of 2,5-dimethyl-7H-thieno[3′,2′:3,4]cyclopenta[1,2-b]thiophene

Step a) 2,2′-dimethyl-4,4′-dithienyl

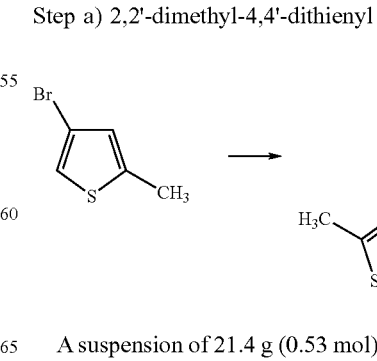

A suspension of 21.4 g (0.53 mol) of Mg in 50 mL of THF was treated with 4 mL (45 mmol) of 1,2-dibromoethane. The mixture starts to warm and the gas starts to bubble. After the evolution of the gas is over, the resulting mixture was treated with the solution of 253 g (1.43 mol) of 4-bromo-2-methylthiophene and 9.5 mL (110 mmol) of dibromoethane in 400 mL of THF. After Mg is dissolved the reaction mixture was allowed to cool to room temperature, treated with 700 mL of THF and with 3.8 g (14.3 mmol) of NiCl$_2$dppp and stirred overnight. The resulting mixture was dried three times with 2 L of 10% aqueous NH$_4$Cl at vigorous stirring, organic phase with suspended crystalline product was isolated, washed twice with 2 L of water and treated with 600 mL of hexane. The suspension was filtered. The product was washed twice with hexane on the filter and dried. Yield of first portion 92 g. The filtrate was isolated, evaporated and recrystallyzed from 1 L of ethanol. Second portion of compound weights 14 g. Total yield of dithienyl 106 g (77%).

$^1$H NMR (CDCl$_3$): 7.08 (d, 1H); 6.98(quintet, 1H); 2.52 (d, 3H)

$^{13}$CNMR (CDCl$_3$): 140.1; 137.1; 124.4; 117.1; 15.3

Step b) 2,5dimethyl-7H-thieno[3',2':3,4]cyclopenta[1,2-b]thiophen-7-one

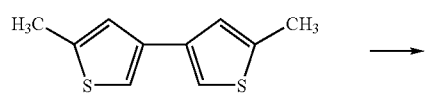

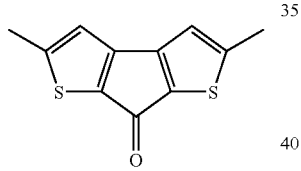

A mixture of 48.6 g (250 mmol) of 2,2'-dimethyl-4,4'-dithienyl, 400 mL of ether and 83 mL (550 mmol) of TMEDA was placed into the bulb, the resulting suspension was cooled to −20° C. and then treated with 250 mL (550 mmol) of 2.2M BuLi in hexane. The mixture was allowed to warm up to r.t. and was stirred for 3 hours. The reaction mixture was treated with 29.3 g (250 mmol) of carbamate (EtO)C(O)NMe$_2$ in 600 mL of ether and then was stirred in 40 hours.

The resulting mixture was poured into 2 L of saturated aqueous solution of NH$_4$Cl under shaking or stirring. Organic phase containing some of the precipitated product was isolated, washed with 1 L of water, treated with 100 mL of hexane and then filtered. The precipitate was washed with water, twice with 100 mL of hexane and dried. Yield of first portion is 31 g. Filtrate was evaporated up to volume of 200 mL to give a suspension. This suspension was filtered, washed with hot hexane and dried. The yield of second portion is 14 g. Total yield 45 g (82%).

$^1$H NMR (CDCl$_3$): 6.58(q, 1H); 2.50 (d, 6H);

$^{13}$C NMR (CDCl$_3$): 178.8; 152.6; 152.2; 133.0; 118.6; 16.1

Step c) Reduction of 2,5-dimethyl-7H-thieno[3',2':3,4]cyclopenta[1,2-b]thiophene

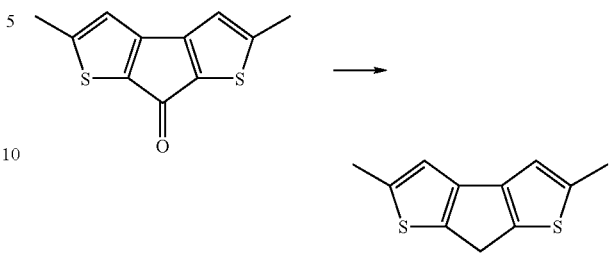

A mixture of 45 g (205 mmol) of 2,5-dimethyl-7H-thieno[3',2':3,4]cyclopenta[1,2-b]thiophen-7-one, 600 mL of diethylene glycol and 70 mL of hydrazine monohydrate was placed into the bulb. The mixture was warmed to 80° C. and kept at this temperature in 1 h at stirring. Then the mixture was intensively refluxed in 1 h, cooled to r.t. treated with solution of 70 g KOH in 230 mL of water. The resulting mixture was carefully heated and the gas started to bubble. The mixture was refluxed for 2 hours, then it was cooled to 70-80° C. and poured into 3 L water. The precipitate was decanted, filtered, washed 7 times with 200-300 mL of water and dried. Yield 32 g (78%).

$^1$H NMR (CDCl$_3$): 6.81 (q, 2H); 3.72 (s, 2H); 2.58 (d, 6H)

$^{13}$C NMR (CDCl$_3$): 143.6; 142.1; 140.1; 116.4; 33.1; 15.9

The yields of the various steps of the process are compared in table 1.

Example 4

Synthesis of 6-(tert-butyl)-2-methyl-8H-indeno[2,1-b]thiophene

Step a) 4-[4-(tert-butyl)phenyl]-2-methylthiophene

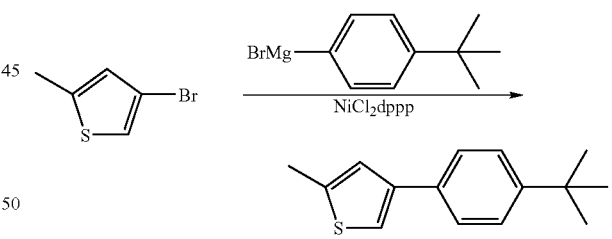

To a mixture of 8.8 g (0.05 mol) of 4-bromo-2-methylthiophene and 0.27 g (0.0005 mol) of NiCl$_2$dppp in 40 mL of ether a solution of para-tBuPhMgBr (prepared from 1.46 g of Mg (0.06 mol) and 12.73 g of para-tBuPhBr (0.06 mol) in 35 mL of ether) was added under stirring at reflux. The reaction mixture was refluxed for additional 3 h and then stirred overnight. The resulting mixture was treated with 10% aqueous NH$_4$Cl, the organic layer was separated, washed with 10% aqueous NH$_4$Cl and then dried over anhydrous Na$_2$SO$_4$. Solvent was evaporated, the residue was recrystallized from methanol. Yield 2.27 g (20%) of colorless crystals.

$^1$H NMR (CDCl$_3$, 30° C.): 7.55 (d, 2H), 7.46 (d, 2H), 7.21 (s, 1H), 7.10 (s, 1H), 2.57 (s,3H), 1.40 (s, 9H).

Step b) 6-(tert-butyl)-2-methyl-8H-indeno[2,1-b]thiophen-8-one

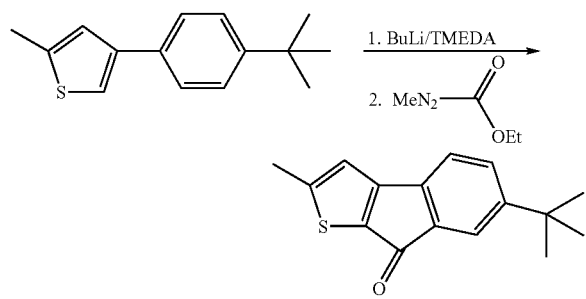

A solution of 2.23 g (0.01 mol) of 4-[4-(tert-butyl)phenyl]-2-methylthiophene, 2.97 mL (0.02 mol) of TMEDA in 30 mL of ether was treated with 13 mL (0.02 mol) of 1.6M BuLi in hexane under stirring at −40° C. Then the reaction mixture was allowed to warm up to r.t. and stirred for 3 h. The reaction mixture was cooled −40° C. and treated with 1.17 g (0.01 mol) of ethyl N,N-dimethylcarbamate in 10 mL of ether. Then the reaction mixture was allowed to warm up to r.t. and was stirred overnight. Resulting mixture was treated with 10% aqueous $NH_4Cl$, organic layer was separated, washed with 10% aqueous $NH_4Cl$ and then dried over anhydrous $Na_2SO_4$. Solvent was evaporated, the residue was washed with methanol. Yield 2.4 g (about 100%) of red oil.
$^1$H NMR ($CDCl_3$, 30° C.): 7.53 (d, 1H), 7.29 (dd, 1H), 7.01 (d, 1H), 6.80 (d, 1H),2.55 (d,3H), 1.33 (s, 9H).

Step c) 6(tert-butyl)-2-methyl-8H-indeno[2,1-b]thiophene

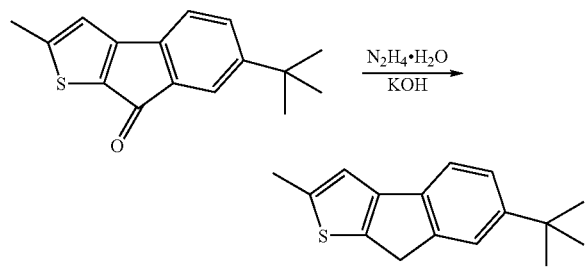

A mixture of 2.40 g (0.0095 mol) of 6-(tert-butyl)-2-methyl-8H-indeno[2,1-b]thiophen-8-one and 2.6 mL (0.05 mol) of hydrazine monohydrate in 25 mL of diethylene glycol was stirred at 80° C. in 40 min and then refluxed for 1 h. The resulting mixture was cooled to r.t., treated with a solution of 2.68 g (0.035 mol) of KOH in 9.4 mL of water and subsequently refluxed for 2 h. The resulting mixture was poured in 150 mL of water, the precipitate was filtered, washed 5 times with 100 mL of water and dried. Yield 1.25 g (54%).
$^1$H NMR ($CDCl_3$, 30° C.): 7.56 (s, 1H), 7.45 (d, 1H), 7.35 (dd, 1H), 6.96 (q, 1H),3.81 (s,2H); 2.60 (d, 3H), 1.42 (s, 9H).

Example 5

Synthesis of 2,5-dimethyl-7H-cyclopenta[1,2-b;3,4-b']dithiophene

Step a) 2,2'-dimethyl-4,4'-dithienyl
In a Schlenk vessel was weighed 5.52 g of Zn-powder (84.75 mmol=1.00 eq), 7.86 g of triphenylphosphine (30.00 mmol=0.35 eq) and 0.84 g of $NiBr_2$ (3.77 mmol=0.04 eq). After flushing the Schlenk vessel with nitrogen, 40 mL of dimethyl formamide was added and the suspension was heated for 30 min at 50° C. The mixture turned to reddish brown during complex formation. To the mixture was added dropwise 15.00 g of 4-bromo-2-methylthiophene (84.75 mmol=1.00 eq) and the mixture was stirred overnight at 50° C. To the dark brown mixture was added 180 mL of cyclohexane. After 5 min stirring at 50° C., 100 mL of aqueous HCl (37%) was added slowly. The mixture was stirred for 30 min at 50° C. and the acidic layer was removed. The cyclohexane layer was extracted again with aqueous HCl (37%). The mixture was kept at 50° C. to prevent precipitation of bis-methylthiophene. The cyclohexane layer was washed twice with water.

The organic layer was collected and the 2,2'-dimethyl-4,4'-dithienyl crystallised at cooling to room temperature. The crystals were collected on a P4 glass filter. Small amounts (1-5%) of side products as phenylmethylthiophene, triphenylphosphine and diphenyl(methylthiophenyl)phosphine were formed during synthesis. Yield=7.29 g. (37.6 mmol), (87.2%), 100% conversion Step b) 2,5dimethyl-7H-thieno[3',2':3,4]cyclopenta[1,2-b]thiophen-7-one
To a solution of 40 g of tetrahydrofuran and 7.7 g (39.7 mmol) of 2,2'-dimethyl-4,4'-dithienyl was added 32.3 mL of BuLi (80.8 mmol) at −20° C. keeping the temperature −6° C. After addition the temperature was kept at −10° C. for 1 h and then for 15 min at room temperature. Then the mixture was cooled to −20° C. and 4.3 g (39.7 mmol) of carbamyl chloride was added keeping the temperature below −6° C. One h after addition the mixture was cooled to −75° C. and was stirred at that temperature for 4 h. Then 5 mL of water was added at that temperature and the cooling bath was removed. At room temperature 100 mL of water was added and the mixture was extracted twice with 50 mL of $CH_2Cl_2$. The organic layer was concentrated and the resulting solid was crystallized from hexane/toluene 90/10 (v/v) yielding 5.7 g of the desired ketone with a purity of ca 99%. Yield 84%

Step c) 2,5-dimethyl-7H-cyclopenta[1,2-b;3,4-b']dithiophene
To a solution of 2.5 g (11.3 mmol) of ketone ex-step b1 in 25 mL of diethylene glycol at 120° C. was added 1.7 g (33.8 mmol) of hydrazine monohydrate. This solution was stirred for 3 h and then 1.9 g (33.8 mmol) of KOH in 6 g of water was added slowly (reflux condenser was used) controlling the gas formation. After 2 h stirring the reaction was complete and workup was done by adding 200 mL of water and filtering off the solid. The solids were washed 5 times with 10 mL of water. After drying 2 g of a brown solid was isolated, being >99% pure 2,5-dimethyl-7H-cyclopenta[1,2-b;3,4-b']dithiophene (85% yield).

Example 6

Synthesis of N-(tert-butyl)(dimethyl)(2-methyl-8H-indeno[2,1-b]thiophen-8-yl)silanamine Zirconium dichloride i) Synthesis of chloro(dimethyl)(2-methyl-8H-indeno[2,1-b]thiophen-8-yl)silane

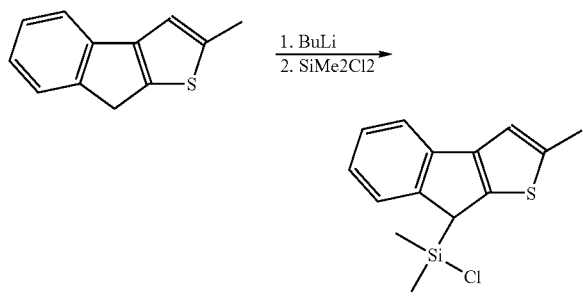

Suspension of 1.86 g (0.01 mol) 2-methyl-8H-indeno[2,1-b]thiophene in 25 mL ether was treated dropwise with 6.25 mL (0.01 mol) of 1.6M BuLi in hexane at −40° C. under stirring. Then the mixture was stirred in additional 3 h. The resulting mixture was treated with 1.20 mL (0.01 mol) of dimethyldichlorosilane in 5 mL of ether at −70° C.; then it was allowed to warm to r.t. and stirred overnight. The solution was isolated and evaporated to give 2.47 g (89%) of the crude product that was used without further purification.

$^1$H NMR (CD$_6$D$_6$, 30° C.) d: 7.57 (m, 2H), 7.33 (t, 1H), 7.18 (t, 1H), 6.85 (m, 1H), 3.78 (s, 1H), 2.32 (s, 3H), 0.10 (s, 3H), 0.08 (s, 3H).

ii) N-(tert-butyl)(dimethyl)(2-methyl-8H-indeno[2,1-b]thiophen-8-yl)silanamine

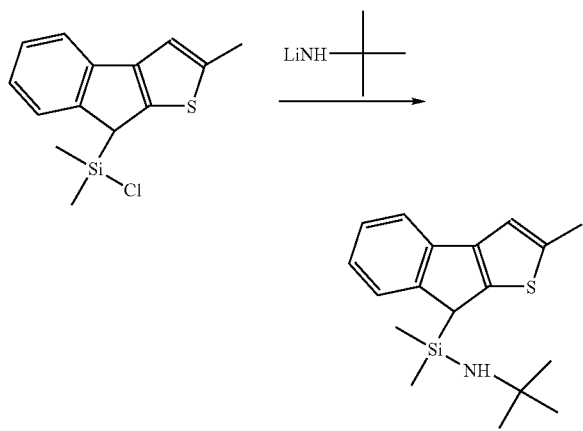

A solution of 0.93 mL (0.0089 mol) of tert-butylamine in 30 mL of ether was treated dropwise with 5.55 mL (0.0089 mol) of 1.6M BuLi in hexane at −30° C. The reaction mixture was stirred at r.t. for 3 h and the resulting suspension was treated with a solution of 2.47 g (0.0088 mol) of chloro(dimethyl)(2-methyl-8H-indeno[2,1-b]thiophen-8-yl)silane in 10 mL of ether at −70° C. The resulting suspension was allowed to warm to r.t. and was stirred overnight. The solution was separated from LiCl and evaporated. The residue was treated with 60 mL hexane, the solution was isolated and evaporated. Yield 1.98 g (71%) of crude product as red oil.

$^1$H NMR (C$_6$D$_6$, 30° C.) d: 7.67 (d, 1H), 7.62 (d, 1H), 7.39 (t, 1H), 7.27 (t, 1H), 6.96 (m, 1H), 3.81 (s, 1H), 2.40 (s, 3H), 1.18 (s, 9H), 0.19 (s, 3H), −0.14 (s, 3H).

iii) N-(tert-butyl)(dimethyl)(2-methyl-8H-indeno[2,1-b]thiophen-8-yl)silanamine Zirconium dichloride

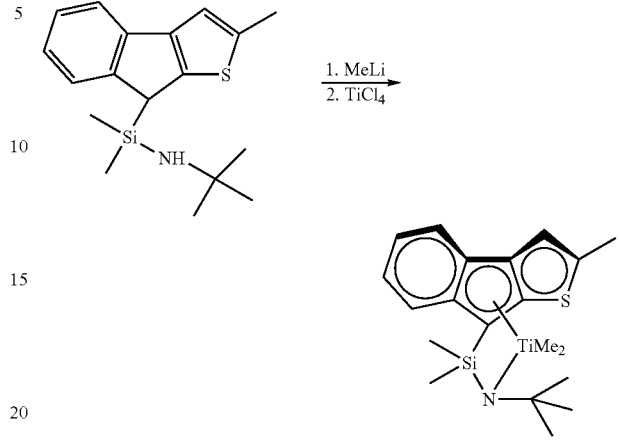

To a solution of 1.98 g (0.0062 mol) N-(tert-butyl)(dimethyl)(2-methyl-8H-indeno[2,1-b]thiophen-8-yl)silanamine in 30 mL of ether 26 mL (0.0312 mol) of 1.2M MeLi in ether was added at −40° C. under stirring. Then the reaction mixture was stirred under reflux for 3 h. The resulting mixture was cooled to −60° C. and a solution of 0.68 mL (0.0062 mol) of TiCl$_4$ in 30 mL of hexane was added. The mixture was allowed to warm to r.t. and was stirred overnight. The resulting mixture was evaporated, the residue was extracted with hexane (3 times with 50 mL).

The hexane solution was concentrated to a volume of 10 mL and kept 10 hours at r.t. The crystalline product was separated from mother solution, wished twice with cold pentane and dried. Yield 0.48 g (20%) of orange crystals.

$^1$H NMR (C$_7$D$_8$, 30° C.) d: 7.57 (d, 1H), 7.49 (d, 1H); 7.12 (dd, 1H); 6.92 (dd,1H);6.71 (q, 1H); 2.24 (d, 3H); 1.43 (s, 9H); 0.63 (s, 3H); 0.61 (s, 3H); 0.32 (s, 3H); −0.06 (s,3H)
$^{13}$C NMR (C$_7$D$_8$, 30° C.) d: 146.8; 141.9; 136.3; 135.9; 128.6; 126.6; 125.2; 125.0; 123.6; 79.5; 58.3; 57.5; 56.9; 34.5; 16.4; 4.5; 4.2

The invention claimed is:

1. A process for preparing a cyclopentadiene derivative having formula (I)

wherein
T$^1$ is selected from the group consisting of oxygen (O), sulphur (S) and NR, wherein R is selected from the group consisting of linear or branched saturated or unsaturated C$_1$-C$_{20}$-alkyl, C$_3$-C$_{20}$-cycloalkyl, C$_6$-C$_{20}$-aryl, C$_7$-C$_{20}$-atkylaryl, and C$_7$-C$_{20}$-arylalky radical, optionally containing heteroatoms belonging to groups 13-17 of the Periodic Table of the Elements;
R$^1$, R$^2$, equal to or different from each other are hydrogen or a linear or branched saturated or unsaturated C$_1$-C$_{20}$-alkyl, C$_3$-C$_{20}$-cycloalkyl, C$_6$-C$_{20}$-aryl, C$_7$-C$_{20}$-alkylaryl or C$_7$-C$_{20}$-arylalkyl radical, optionally containing heteroatoms belonging to groups 13-17 of the Periodic Table of the Elements; or they can form a $C_4$-$C_7$ ring optionally containing O, S, N, P or Si atoms that can bear substituents;

W is a moiety of formula (a) or (b)

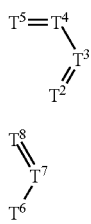

(a)

(b)

wherein $T^2$, $T^3$, $T^4$, $T^5$ equal to or different from each other are selected from the group consisting of nitrogen (N) and $CR^3$ wherein $R^3$ is hydrogen or a linear or branched saturated or unsaturated $C_1$-$C_{20}$-alkyl, $C_3$-$C_{20}$-cycloalkyl, $C_6$-$C_{20}$-aryl, $C_7$-$C_{20}$-atkylaryl or $C_7$-$C_{20}$-arylalkyl radical, optionally containing heteroatoms belonging to groups 13-17 of the Periodic Table of the Elements; or two adjacent $R^3$ groups can form a $C_4$-$C_7$ ring optionally containing O, S, N, P or Si atoms, wherein said ring can bear substituents;

$T^6$ has the same meaning as $T^1$;

$T^7$ and $T^8$ equal to or different from each other are selected from N and $CR^3$ wherein $R^3$ is hydrogen or a linear or branched saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; optionally two adjacent $R^3$ groups can form a $C_4$-$C_7$ ring optionally containing O, S, N, P or Si atoms, said ring can bear substituents; with the proviso that when $T^6$ is different from NR, $T^7$ and $T^8$ are both $CR^3$;

said process comprising the following steps:

a) reacting a compound of formula (II)

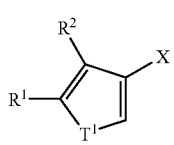

(II)

with a compound of formula (III)

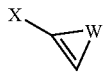

(III)

in the presence of a coupling system, wherein X is selected from the group consisting of chlorine, iodine, and bromine; thereby forming a compound of formula (IV)

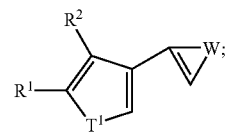

(IV)

b) contacting the compound of formula (IV) with a carbonylating system; thereby forming a compound of formula (IVa)

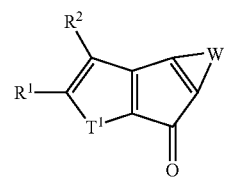

(IVa)

and;

c) treating the compound of formula (IVa) with a reducing agent.

2. The process according to claim 1 for preparing the cyclopentadiene compounds of formula (Ia)

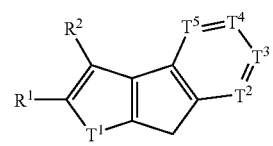

(Ia)

comprising the following steps:

a) reacting the compound of formula (II)

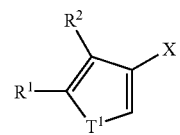

(II)

with a compound of formula (V)

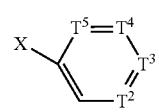

(V)

in the presence of a coupling system, wherein X is selected from the group consisting of chlorine, iodine, and bromine; thereby forming a compound of formula (VI)

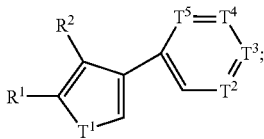
(VI)

b) contacting the compound of formula (VI) with a carbonylating system; thereby forming a compound of formula (VIa)

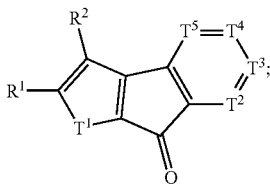
(VIa)

and c) treating the compound of formula (VIa) with a reducing agent and recovering the product.

3. The process according to claim 1 wherein $T^1$ is sulphur or oxygen; $T^2$ is $NCH_3$ or CH; $T^3$, $T^4$, $T^5$ are CH; $R^1$ and $R^2$ are selected from the group consisting of hydrogen, methyl, ethyl, phenyl, and trimethylsilyl, or together form a benzene ring.

4. The process according to claim 1 for preparing the cyclopentadiene compounds of formula (Ib)

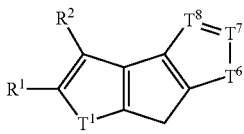
(Ib)

comprising the following steps:

a) reacting the compound of formula (II)

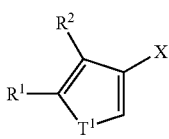
(II)

with a compound of formula (VII)

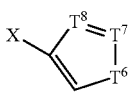
(VII)

in the presence of a coupling system, wherein X is selected from the group consisting of chlorine, iodine, and bromine; thereby forming a compound of formula (VIII)

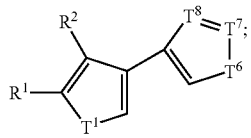
(VIII)

b) contacting the compound of formula (VIII) with a carbonylating system; thereby forming a compound of formula (VIIIa)

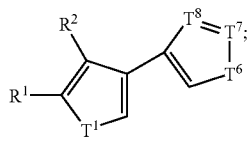
(VIII)

c) treating the compound of formula (VIIIa) with a reducing agent and recovering the product.

5. The process according to claim 4 wherein $T^1$ and $T^6$ are the same and they are sulfur or oxygen; $T^7$ and $T^8$ equal to or different from each other are $CR^3$; and $R^1$ and $R^2$ are hydrogen, methyl, ethyl, phenyl, trimethylsilyl group or together form a benzene ring.

6. The process according to claim 1 wherein step a) comprises the following substeps:

i) contacting the compound of formula (II) with magnesium to form a corresponding Grignard reagent; and
 ii) contacting the Grignard reagent formed in step i) with the compound of formula (III) in the presence of a compound selected from the group consisting of [1,3-bis(diphenylphosphino)propane]dichloronickel (dppp-NiCl2), [1,1'-bis(diphenylphosphino)ferrocene]dichloropalladium (dppfPdCl2), and tetrakis(triphenylphosphino)palladium.

7. The process according to claim 1 wherein step a) comprises the following substeps:

i) contacting the compound of formula (III) with magnesium to form a corresponding Grignard reagent; and
 ii) contacting the Grignard reagent formed in step i) with the compound of formula (II) in the presence of a compound selected from the group consisting of [1,3-bis(diphenylphosphino)propane]dichloronickel (dppp-NiCl2), [1,1'-bis(diphenylphosphino)ferrocene]dichloropalladium (dppfPdCl2), and tetrakis(triphenylphosphino)palladium.

8. The process according to claim 1 wherein step b) comprises the following substeps:

i) contacting the compound of formula (IV) with two equivalents of a base, thereby forming a dianionic compound; and
 ii) treating the dianionic compound with a compound of formula (IX)

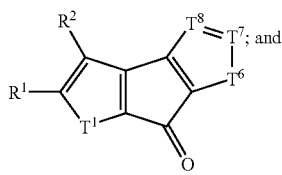

(VIIIa)

wherein $R^4$ and $R^5$ equal to or different from each other are selected from the group consisting of hydrogen, chlorine, bromine, iodine, OR and N(R)2.

9. The process according to claim 8 wherein in the compound of formula (IX), $R^4$ is chlorine, bromine, iodine, $CF_3$, $Cl_3$ or OR; and $R^5$ is selected from the group consisting of $CF_3$, $Cl_3$, OR and N(R)2.

10. The process according to claim 1 wherein step b) comprises the following substeps:
  i) contacting the compound of formula (IV) with two equivalent of a base and subsequently with one equivalent of a compound selected from chlorine, bromine or iodine; thereby forming an anionic monohalogenated derivative; and
  ii) treating the anionic monohalogenated derivative obtained from step i) with a compound of formula (IXa)

$$[M_mL_j(CO)_n]^a \quad (IXa)$$

wherein M is a transition metal of groups 4-11 of the periodic table; L is a ligand that coordinates the metal M that can be neutral or with a positive or negative charge; a ranges from −4 to +4 and represents the charge of the complex; wherein when a is 0 the complex is neutral; m ranges from 1 to 20; j ranges from 0 to 30; and n ranges from 1 to 50.

11. The process according to claim 1 wherein step b) comprises the following substeps:
  i) contacting the compound of formula (IV) with a halogenating compound and subsequently with one equivalent of a base; thereby forming an anionic monohalogenated derivative; and
  ii) treating the anionic monohalogenated derivative with a compound of formula (IXa)

$$[M_mL_j(CO)_n]^a \quad (IXa)$$

wherein M is a transition metal of groups 4-11 of the periodic table; L is a ligand that coordinates the metal M that can be neutral or with a positive or negative charge; a ranges from −4 to +4 and represents the charge of the complex; wherein when a is 0 the complex is neutral; m ranges from 1 to 20; j ranges from 0 to 30; and n ranges from 1 to 50.

12. The process according to claim 4 wherein the compounds of formula (II) and (VII) are the same and the coupling system comprises:
  i) an alkali or alkaline earth-metal;
  ii) a compound of formula $Q(G)_3$ or a compound of formula $(G)_2Q\text{-}A\text{-}Q(G)_2$ wherein Q is a phosphorus or nitrogen atom, G equal to or different from each other are selected from the group consisting of linear or branched saturated or unsaturated $C_1\text{-}C_{20}$-alkyl, $C_3\text{-}C_{20}$-cycloalkyl, $C_6\text{-}C_{20}$-aryl, $C_7\text{-}C_{20}$-alkylaryl, and $C_7\text{-}C_{20}$-arylalkyl radical, optionally containing heteroatoms belonging to groups 13-17 of the Periodic Table of the Elements and A is a group linking the two Q atoms chosen from a divalent organic radical selected from the group consisting of $C_1\text{-}C_{20}$-alkylene, $C_3\text{-}C_{20}$-cycloalkylene, $C_2\text{-}C_{20}$-alkenylene, $C_6\text{-}C_{20}$-arylene $C_7\text{-}C_{20}$-alkylarylene, and $C_7\text{-}C_{20}$-arylalkylene divalent radical, optionally containing heteroatoms belonging to groups 13-17 of the Periodic Table of the Elements, or a complex that has the two radicals Q(G)2 as substituents; and
  iii) a transition metal halogenide of formula $JZ_e$ wherein J is a transition metal; Z is chlorine, bromine, or iodine; and e is equal to the oxidation state of the metal J.

13. The process according to claim 12 wherein the coupling system comprises:
  i) Zinc powder or granules;
  ii) triphenylphosphine; and
  iii) $NiBr_2$.

14. The process according to claim 11 wherein the base used in step b) is selected from hydroxides and hydrides of alkali- and alkaline-earth metals, metallic sodium and potassium and organometallic lithium compounds.

15. The process according to claim 1 wherein the reduction step c) comprises the following substeps:
  i) contacting the compound of formula (IV) with $N_2H_4$;
  ii) adding a solution of KOH in water; and
  iii) filtering the solid and recovering the product.

16. The process according to claim 1, wherein X is bromine.

17. The process according to claim 2, wherein X is bromine.

18. The process according to claim 12, wherein J is a transition metal of groups of the Periodic Table.

* * * * *